(12) United States Patent
Pielak et al.

(10) Patent No.: US 8,773,130 B2
(45) Date of Patent: Jul. 8, 2014

(54) DEVICE FOR PARTICULATE NMR SAMPLES IN A FLUID AND RELATED METHODS

(75) Inventors: Gary J. Pielak, Chapel Hill, NC (US); Christopher Barnes, Huntersville, NC (US); Naima G. Sharaf, North Andover, MA (US); Gregory Young, Hillsborough, NC (US); Freddy Pinero, Durham, NC (US); Lisa Charlton, Pittsburgh, PA (US); Christopher Seagle, Medford, MA (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 450 days.

(21) Appl. No.: 13/260,975

(22) PCT Filed: Mar. 31, 2010

(86) PCT No.: PCT/US2010/029297
§ 371 (c)(1),
(2), (4) Date: Nov. 16, 2011

(87) PCT Pub. No.: WO2010/120498
PCT Pub. Date: Oct. 21, 2010

(65) Prior Publication Data
US 2012/0062226 A1 Mar. 15, 2012

Related U.S. Application Data

(60) Provisional application No. 61/165,640, filed on Apr. 1, 2009.

(51) Int. Cl.
*G01V 3/00* (2006.01)

(52) U.S. Cl.
USPC .................................................. 324/309

(58) Field of Classification Search
USPC .................................................. 324/300–322
See application file for complete search history.

(56) References Cited

U.S. PATENT DOCUMENTS

| | | | | |
|---|---|---|---|---|
| 4,173,775 A | * | 11/1979 | Kneip, Jr. | 361/141 |
| 4,259,638 A | * | 3/1981 | Krueger | 324/306 |
| 6,305,190 B1 | * | 10/2001 | Driehuys et al. | 62/637 |

(Continued)

OTHER PUBLICATIONS

International Search Report and the Written Opinion for PCT/US2010/029297 mailed on Oct. 26, 2010.
Sina Reckel et al.; "In-Cell NMR Spectroscopy"; Progress in Nuclear Magnetic Resonance Spectroscopy 51 (2007) 91-101.

(Continued)

*Primary Examiner* — Dixomara Vargas
(74) *Attorney, Agent, or Firm* — Myers Bigel Sibley & Sajovec, PA

(57) ABSTRACT

Devices and related methods for nuclear magnetic resonance (NMR) analysis of particulate materials are provided including a detector chamber configured for insertion into an NMR spectrometer and configured to receive particulate materials in a fluid. A circulation chamber is attached to and in fluid communication with a first end of the detector chamber. A transition region is between the detector chamber and the circulation chamber, and a fluid supply interface is at a second end of the detector chamber that is configured to attach to a fluid source. The detector chamber, the circulation chamber and the transition region are sized and configured such that, when fluid flows from the fluid supply interface into the second end of the detector region, a circulating current is formed in the transition region and/or the circulation chamber such that the particulate matter is contained in the circulation chamber by the circulating current.

16 Claims, 9 Drawing Sheets

(56) References Cited

U.S. PATENT DOCUMENTS

| | | | |
|---|---|---|---|
| 7,511,496 B2 * | 3/2009 | Schiano | 324/312 |
| 8,583,200 B2 * | 11/2013 | Harrison | 505/160 |
| 2004/0039280 A1 | 2/2004 | Wu | |
| 2005/0124867 A1 | 6/2005 | Kjaer | |
| 2006/0173284 A1 | 8/2006 | Ackerman | |

OTHER PUBLICATIONS

Jean-Philippe Grivet et al.; "NMR for microbiology: in vivo and in situ applications"; Progress in Nuclear Magnetic Resonance Spectroscopy xxx (2008), 1-53.

Jean-Philippe Grivet et al.; "NMR for microbiology: in vivo and in situ applications"; Progress in Nuclear Magnetic Resonance Spectroscopy 54 (2009) 1-53.

* cited by examiner

DEVICE FOR PARTICULATE NMR SAMPLES IN A FLUID AND RELATED METHODS

GOVERNMENT LICENSE RIGHTS

This invention was made with government support under National Institutes of Health grant no. 5-DP1-OD000783 and National Science Foundation grant no. MCB-0516547. The government has certain rights in the invention.

RELATED APPLICATIONS

This application is a national phase application under 35 U.S.C. §371 of PCT Application No. PCT/US2010/029297, filed Mar. 31, 2010, which claims priority to U.S. Provisional Application No. 61/165,640, filed Apr. 1, 2009, the disclosures of which are hereby incorporated by reference in their entireties.

FIELD OF THE INVENTION

The present invention relates to nuclear magnetic resonance (NMR), and in particular, to NMR for particulate NMR samples in a fluid environment.

BACKGROUND

Nuclear magnetic resonance (NMR) spectroscopy is a technique that utilizes the magnetic properties of nuclei to obtain information about the physical, chemical, electronic and structural properties of molecules. When placed in a magnetic field, certain NMR active (such as $^1$H and $^{13}$C) are aligned with the field. This alignment can be perturbed using an alternating magnetic field that is generally orthogonal to the main field. The alternating magnetic field is typically administered by a radio frequency (RF) coil that is proximate the sample. After the alternating magnetic field is terminated, a signal can be collected by the RF coil due to a current induced in the RF coil as the nuclei in the sample "relax" or realign with the primary magnetic field.

NMR spectroscopy has been used to study living cells, which can be immobilized inside a semi-permeable encapsulate and suspended in a fluid. One potential difficulty in NMR spectroscopy is to maintain cells in a high density in the suspension for the amount of time desired to obtain a spectrum while maintaining the viability of the cells. The cells typically have relatively low NMR sensitivity, and consequently the cells may be placed in an NMR sample chamber with high concentrations in an effort to achieve higher NMR signals. However, it may be difficult to sustain the viability of living cells in the sufficiently high densities that may be desirable for high NMR signal strength.

NMR sample chambers have been developed in an effort to maintain a high density of cells to reduce signal acquisition times while also attempting to maintain cell viability. For example, NMR sample tubes have been designed to provide unidirectional flow of fluid, such as a perfusion medium including oxygen and/or glucose for maintaining cell viability. The fluid exits the sample tube through a filter, which is sized to generally prevent the cells from also exiting the sample tube. Although the fluid flow operates to compact the encapsulated cells in the NMR tube and supply oxygen and/or glucose, these systems may have problems associated with filter clogging. In addition, the encapsulated cells may be in such close proximity to one another that cell viability may be difficult to achieve.

SUMMARY

According to some embodiments of the present invention, a device for nuclear magnetic resonance (NMR) analysis of particulate materials is provided. The device includes a detector chamber configured for insertion into an NMR spectrometer and configured to receive particulate materials in a fluid. The detector chamber has a first end and a second end. A circulation chamber is attached to and in fluid communication with the first end of the detector chamber. A transition region is between the detector chamber and the circulation chamber, and a fluid supply interface is at the second end of the detector chamber that is configured to attach to a fluid source. The detector chamber, the circulation chamber and the transition region are sized and configured such that, when fluid flows from the fluid supply interface into the second end of the detector region, a circulating current is formed in the transition region and/or the circulation chamber such that the particulate matter is contained in the circulation chamber by the circulating current.

In some embodiments, the circulating current substantially prevents particulate material from entering the detector chamber when fluid flows from the fluid supply interface. The fluid flowing from the fluid supply interface may form a reduced pressure region in the transition region and/or the circulation chamber. The detector chamber may be sized and configured such that, when a fluid in the detector chamber is generally static, the particulate material is contained in the detector chamber.

In some embodiments, the particulate material is an encapsulated cell and the fluid is a perfusion medium.

In some embodiments, the fluid supply interface is configured to connect to a pump that supplies fluid from the fluid source to the detector chamber to form the reduced pressure region. The circulation chamber may have a cross-sectional area that is larger than a cross-sectional area of the detector chamber. The transition region may connect the circulation chamber and the detector chamber at an angle between about 30 and 60 degrees.

In some embodiments, a method for NMR imaging of particulate matter in a fluid is provided. A device is provided including a detector chamber configured for insertion into an NMR spectrometer and configured to receive particulate materials in a fluid. The detector chamber has a first end and a second end. A circulation chamber is attached to and is in fluid communication with the first end of the detector chamber, and a transition region is between the detector chamber and the circulation chamber. A fluid supply interface at the second end of the detector chamber is configured to attach to a fluid source. A nuclear magnetic resonance (NMR) signal is acquired from particulate material in the detector chamber. Fluid flow is supplied into the second end of the detector region to form a circulating current in the transition region and/or the circulation chamber such that the particulate matter is contained in the circulation chamber by the circulating current.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 6A is an in-cell HSQC spectrum of alginate encapsulated *E. coli* expressing α-synuclein in the bioreactor. FIG. 6B is an in-cell HSQC spectrum of *E. coli* expressing α-synuclein. FIG. 6C is an in vitro HSQC spectrum of 200 lM purified wild type α-synuclein in 0.1 M HEPES buffer, pH 7.2 at 10° C. FIG. 6D is an in-cell HSQC spectrum of alginate encapsulated *E. coli* expressing α-synuclein. The spectra shown in FIGS. 6A, 6B and 6D were acquired at 37° C. The spectra in FIGS. 6B-6D were acquired in a 5 mm NMR tube using a 5 mm probe. The spectrum in FIG. 6A was acquired in the 8 mm bioreactor using an 8 mm probe.

FIG. 7A is a spectrum collected before induction, FIG. 7B is a spectrum collected four hours post induction, FIG. 7C is eighteen hours post induction, and FIG. 7D is a spectrum of the spent medium.

FIG. 8A is an in-cell SOFAST 15N-1H HMQC spectrum of the defined phosphate-free minimal media. FIG. 8B is a spectrum of $^{15}N$ enriched encapsulated *E. coli* cells containing the control pUC18 plasmid. FIG. 8C is a spectrum of encapsulated *E. coli* expressing α-synuclein. FIG. 8D is an overlay of the spectra [medium (dashed outlines), puc18 control cells (solid outliens), and α-synuclein (grey-scale)]. Crosspeaks used in subsequent analysis are labeled a-h. Spectra were acquired in the 8 mm bioreactor using an 8 mm probe at 37° C.

FIGS. 9A-9E shows α-synuclein crosspeaks, FIGS. 9F-9G shows metabolite crosspeaks. FIG. 9H shows crosspeaks from the defined phosphate-free minimal media. Crosspeak volumes are normalized to the largest volume and are labeled in FIG. 8D. Error bars represent the standard error from three independent experiments.

DETAILED DESCRIPTION OF EMBODIMENTS OF THE INVENTION

Figure 1:
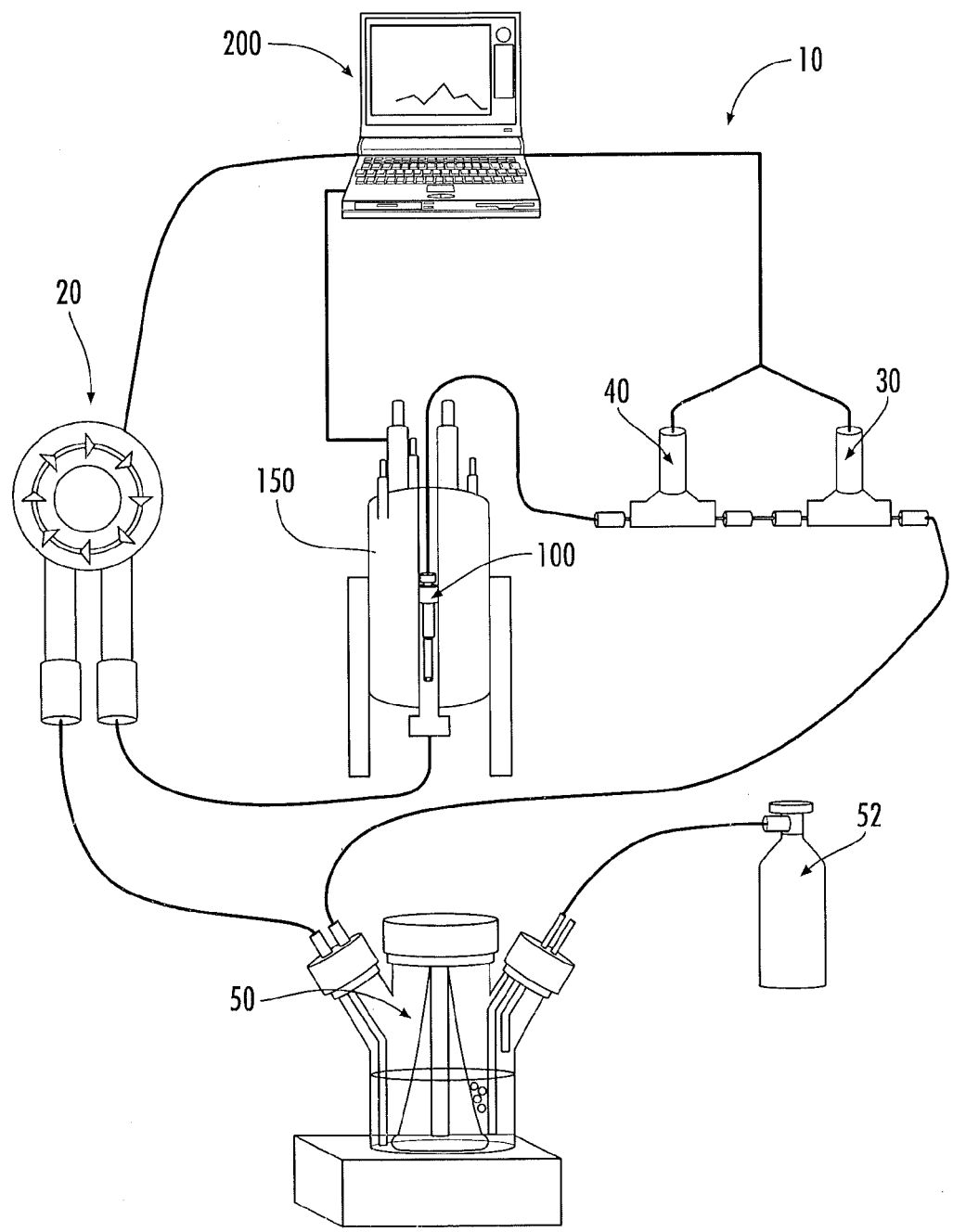
FIG. 1 is a schematic diagram of a system for nuclear magnetic resonance (NMR) analysis of a fluid having a particulate material therein according to embodiments of the present invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms; such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

As illustrated in FIG. 1, a system 10 for NMR analysis of particulate materials, such as encapsulated cells, is shown. The system 10 includes a sample device 100 for containing the particulate materials in a fluid medium. The sample device 100 is configured for at least partial insertion into an NMR detection apparatus (not shown). The sample device 100 includes a fluid inlet I and a fluid outlet O. The inlet I is connected to a pump 20 and the outlet O is connected to optional sensors, such as an oxygen probe 30 and a pH probe 40, for monitoring and detecting characteristics of the fluid medium in the sample device 100. A fluid source 50 is connected to the inlet I via the pump 20 such that fluid from the fluid source 50 can be pumped by the pump 20 into the inlet I. In some embodiments, the fluid source 50 is a perfusion or cell-growth medium, such as luria broth for prokaryotic cells or Ham's F12 medium for eukaryotic cells, and the fluid source 50 can be purged with a mixture of gases from a gas source 52. A controller 200, such as a microprocessor, controls the activation of the pump 20 and/or collects data from the probes 30, 40. In some embodiments, the sample device 100 is at least partially inserted into an NMR detection apparatus 150, and the controller 200 controls the operation of the pump 20 and the NMR detection apparatus as described herein.

Figure 2:
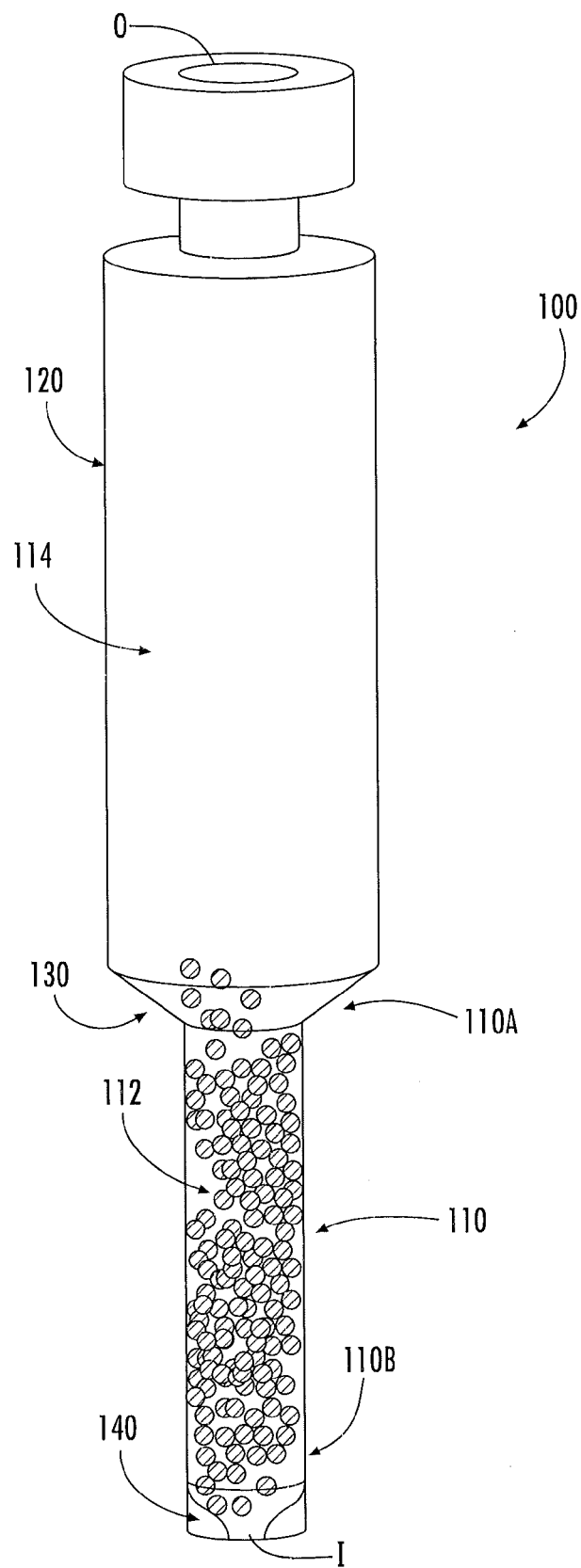
FIG. 2 is a schematic diagram of a device for containing the particulate materials in a fluid medium in which the particulate material is settled in a detector chamber.
Figure 3:
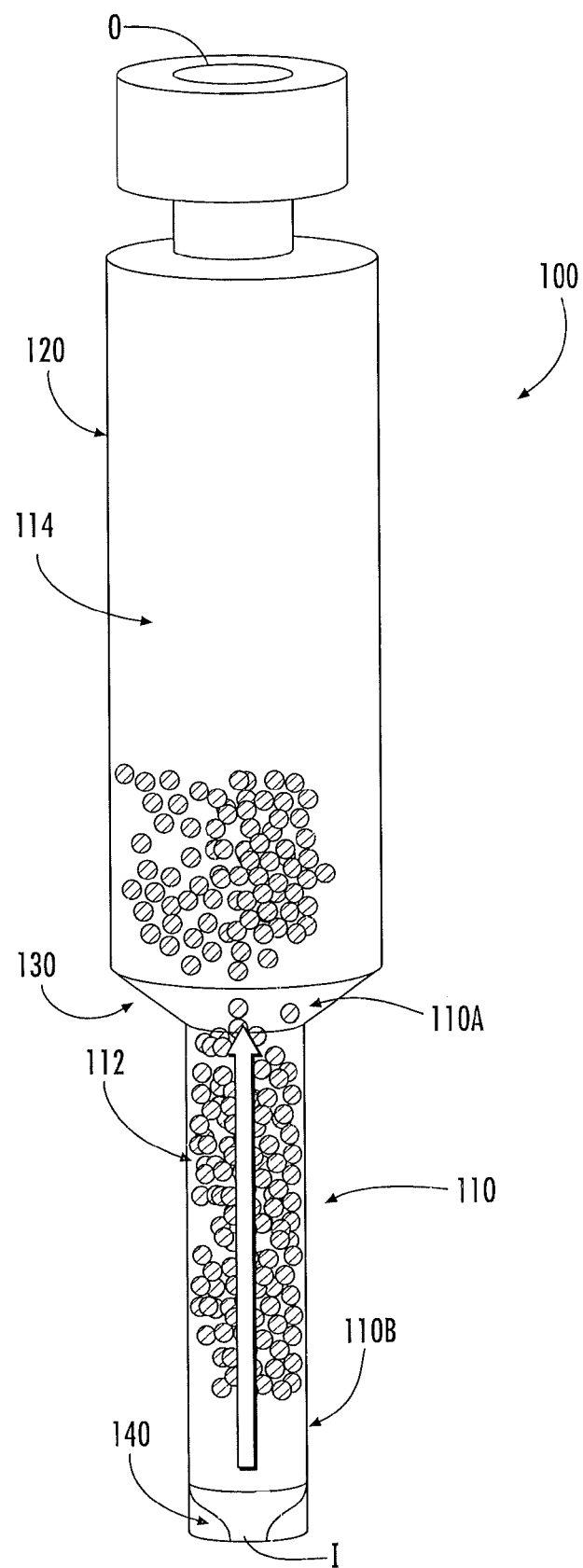
FIG. 3 is a schematic diagram of the device of FIG. 2 in which a fluid is pumped into the detector chamber so that the particulate material travels into a circulation chamber.
Figure 4:
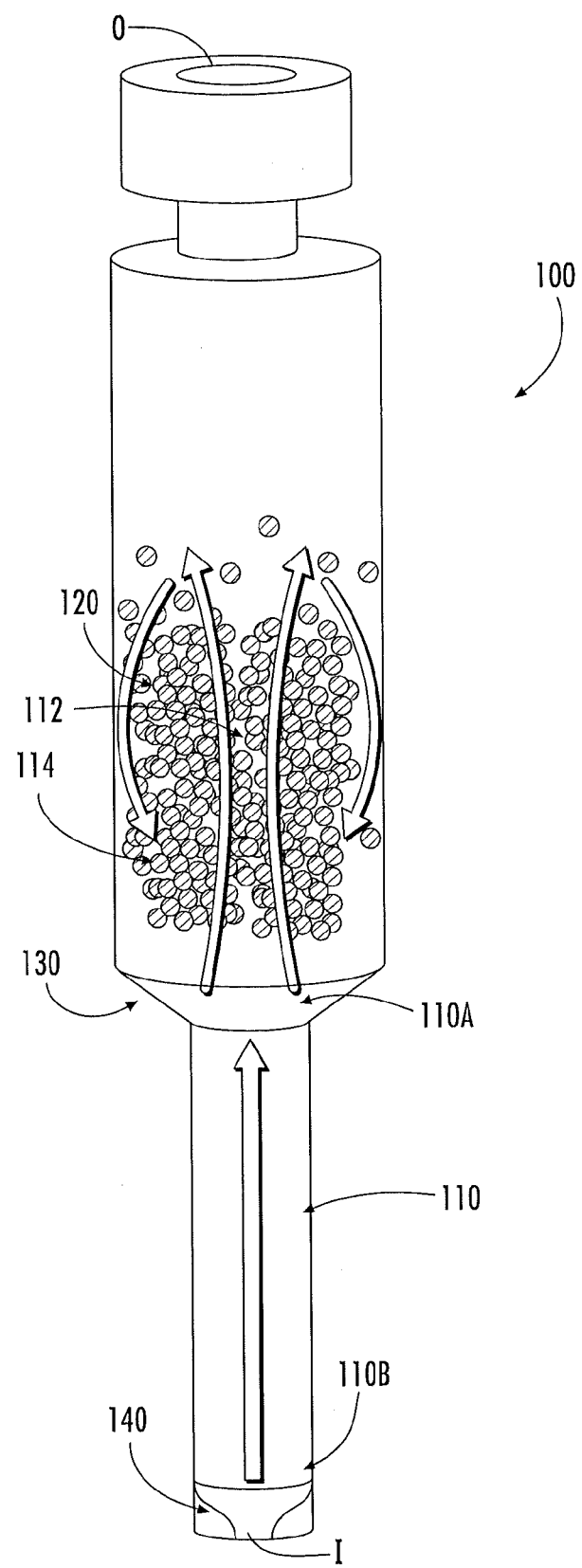
FIG. 4 is a schematic diagram of the device of FIG. 2 in which the particulate material is contained within the circulation chamber.

As shown in FIGS. 2-4, the device 100 includes a detector chamber 110 configured for insertion into an NMR spectrometer 150. The detector chamber 110 is configured to receive particulate material 112 in a fluid 114. As illustrated, the detector chamber 110 has two ends 110A and 110B. The circulation chamber 120 is attached to and is in fluid communication with the first end 110A of the detector chamber 110. A transition region 130 is between the detector chamber 110 and the circulation chamber 120. A fluid supply interface 140 is at the second end 110B of the detector chamber 110, and the fluid supply interface 140 provides an inlet I that is configured to attach to a pump as shown in FIG. 1. The fluid supply interface 140, the inlet I and/or the outlet O can include a filter or membrane that is configured to permit fluid flow into and out of the device 110 and to reduce or prevent the passage of the particulate material 112.

When the fluid 112 in the detector chamber 110 is generally static, the particulate material 112 is contained in the detector chamber 110 as shown in FIG. 2. The detector chamber 110, the circulation chamber 120, and the transition region 130 are sized and configured such that, when fluid 114 flows from the inlet I of the fluid supply interface 140 into the second end 110B of the detector chamber 110, the particulate material 112 travels from the detector chamber 110 to the circulation chamber 120 via the transition region 130 as shown in FIG. 3. The particulate material 112 is contained in the circulation chamber 120 and/or transition region 130 as fluid flows from the fluid supply interface 140 and forms counter-rotating currents as shown in FIG. 4.

Without wishing to be bound by any one theory and with reference to FIGS. 2-4, the detector chamber 110, the circulation chamber 120 and the transition region 130 therebetween can be sized and configured to form a reduced pressure region in the circulation chamber 120 and/or the transition region 130 such that the particulate material 112 is contained in the circulation chamber 120 and/or the transition region 130 during fluid flow as shown in FIGS. 3-4. When fluid flows from the fluid supply interface 140 into the detector chamber 110, the fluid velocity is higher through the detection chamber 110 than in the circulation chamber 120 due to the smaller cross-sectional area (or diameter) of the detection chamber 110 compared with the circulation chamber 120. Consequently, the center portion of the circulation chamber 120 has a lower pressure due to the higher fluid flow rate compared to the outer portion of the circulation chamber 120. The pressure differential forms rotating current flow as shown in FIG. 4 and maintains the particulate material 112 in the circulation chamber 120 when fluid is flowing into the fluid supply interface 140.

In some embodiments, a circulation current (i.e., a generally rotating current) is formed in the transition region 130 and/or circulation chamber 120 that maintains the particulate material 112 in a region of the device 100. Specifically, the particulate material 112 circulates in fluid currents in the circulation chamber 120 such that the particulate material 112 is pushed upward by the fluid flowing from the detection chamber 110 in the center portion of the circulation chamber 120. The particulate material 112 subsequently falls downward when the particulate material 112 is in the outer portion of the circulation chamber 120. However, the particulate material 112 generally does not fall back into the detector chamber 110 due to the upward fluid flow in the central portion of the circulation chamber 120 and the transition region 130. As shown in FIG. 4, the current forms a counter-rotating flow pattern that generally maintains the particulate material 112 in the circulation chamber 120.

In this configuration, the viability of the cells can be increased by periodically initiating fluid flow from the fluid supply interface 140 to cause the particulate material 112 to travel into and be contained in the circulation chamber 120 as shown in FIGS. 3-4. The fluid can include a perfusion medium, such as glucose and/or oxygen, to maintain cell viability. In some embodiments, the fluid flow from the fluid supply interface 140 as shown in FIGS. 3-4 can be performed when NMR spectra are not being acquired. Thus, the viability of the cells can be maintained by periodically circulating the cells into the circulation chamber 120. When NMR spectra are being acquired, the particulate material 112 can be maintained with high concentration in the detection chamber 110, for example, by maintaining the fluid flow at a generally static state as shown in FIG. 2. As illustrated, the particulate material 112 settles into the detection chamber 110 due to gravitational forces. However, it should be understood that fluid can also be pumped in a direction toward the second end 110B of the chamber 110 to maintain a relatively high concentration of particulate material 112.

Figure 5:
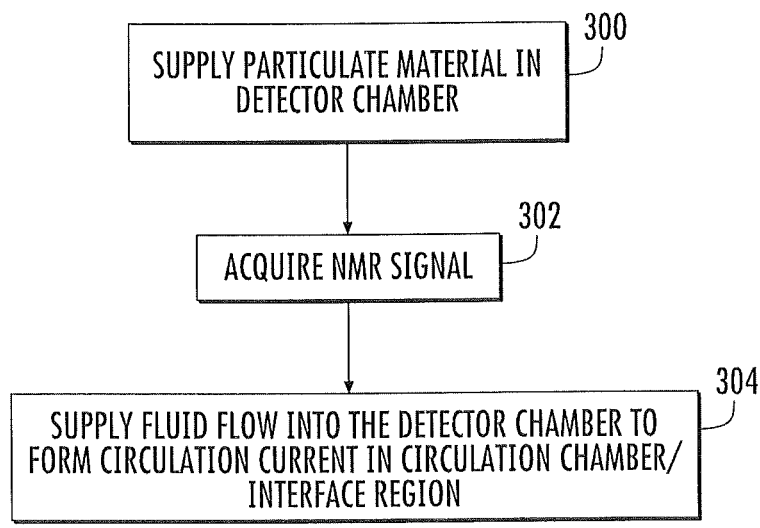
FIG. 5 is a flowchart illustrating operations according to some embodiments of the present invention.

As illustrated in FIG. 5, a particulate material can be supplied to a detection chamber, such as the detection chamber 110 of the device 100 of FIGS. 1-4 (Block 300). An NMR signal can be acquired when the particulate material is in the detection chamber in a relatively high concentration (Block 302). A fluid flow is supplied to the detection chamber to form a circulation current in the circulation chamber and/or transition region, such as the circulation chamber 120 and transition region 130 of FIGS. 1-4 (Block 304). The circulation current maintains the particulate material in the circulation chamber and/or transition region as described herein. It should be understood that the order of Blocks 302 and 304 can be reversed, and/or the steps can be repeated as desired for a given experiment.

In some embodiments, the particulate material 112 of FIGS. 1-4 are encapsulated cells, such as *Escherichia coli*, Chinese Hamster ovarian cells, HeLa. The cells can be encapsulated or trapped in an encapsulation medium, such as agarose gels, alginate beads, and/or silica gels. The fluid 114 can be a perfusion medium, such as a fluid including glucose and/or oxygen, luria broth, Ham's F12 medium, BioExpress 1000 Rich Medium for bacterial growth and the like. Gas mixtures can also be used, including 95% air and 5% carbon dioxide.

In particular embodiments, the transition region 130 provides an angled interface between the detection chamber 110 and the circulation chamber 120 to facilitate the fluid flow shown in FIG. 4 such that the particulate material 112 is contained within the circulation chamber 120. For example, the transition region 130 can form an angle between the detection chamber 120 and the circulation chamber 130 of between about 30 and 60 degrees, or in some embodiments, about 45 degrees such that the cells can be able to fall into the detection chamber 110 during fluid flow. Exemplary fluid flow rates into the detection chamber 110 for maintaining the particulate material 112 in the circulation chamber 120 as shown in FIG. 4 are between about 45 and 55 mL/min. However, it should be understood that the fluid flow rates can vary depending on the size of the particulate material 112. For example, for encapsulated cells ranging from about 550-675 µm, a flow rate of about 48 mL/min can be used. Larger encapsulated cells or other particulate materials may require faster flow rates, such as about 60 mL/min or more.

The detector chamber 110 can be sized and configured to be inserted into an NMR spectrometer, such as Varian, Bruker, and/or JEOL spectrometers. Although embodiments according to the invention are described herein with respect to NMR spectrometers, it should be understood that bioreactors according to embodiments of the invention can be used in other spectrometers or to maintain the viability of cells over extended periods of time for other types of relatively long term experiments.

Embodiments according to the present invention will now be described with respect to the following non-limiting examples.

EXAMPLES

The CEC Bioreactor

The bioreactor is made from Teflon to facilitate NMR experiments involving $^1H$ detection and functions as illustrated with respect to the exemplary device shown in FIGS. 2-4. Alternatively, a bioreactor may be formed from Plexiglass or other suitable materials. A Plexiglass bioreactor, for example, has been made for $^{19}F$ detection. The bioreactor is designed for an 8 mm probe to facilitate fabrication with conventional machine tools. The bioreactor comprises three main parts: an 8 mm diameter tube, a circulation chamber, and an adjustable threaded cap outlet. An inlet for an Upchurch Scientific Super Flangeless Fitting is located on the upper part of the outlet. A 1/1600 OD inlet for Upchurch Scientific perfluoro alkoxy alkane tubing is located at the bottom.

The experimental setup is similar to that shown in FIG. 1; however, the oxygen probe 30 is omitted, and the pH probe 40 is used. In addition, the liquid sample media was temperature regulated by a water bath between the device 100 and the pump 20. The liquid media is contained in a 1 L Corning three neck spinner flask with a tubing adaptor on one side arm. The pump 20 is a peristaltic MasterFlex pump and moves the media at a rate of 45 ml/min from the flask, through the tubing adaptor, and into the PFA tubing. The tubing runs from the pump 20 into the bottom of an 8 mm Varian triple resonance z-gradient probe through an opening created by removing a heater. The temperature is controlled with the spectrometer's FTS Systems heating apparatus (Model TC-84). PFA tubing between the pump 20 and the bioreactor device 100 is placed in a Fisher Scientific Isotemp water bath to warm the media, which flows from the bottom of the bioreactor device 100 as illustrated in FIGS. 2-4. The PFA tubing at the top of the bioreactor device 100 returns the media, via a pH probe 40, to the 1 L the Corning three neck spinner flask. The pH probe 40, pump 20 and NMR spectrometer apparatus 150 are connected to a laptop computer or controller 200. The $^1H$-$^{15}N$ band-selective optimized flip-angle short transient (SOFAST) heteronuclear multiple quantum coherence (HMQC) pulse program provided in the Varian Biopak suite of pulse sequences was modified to send voltage outputs to the computer. See P. Schanda, B. Brutscher, Very fast two-dimensional NMR spectroscopy for real-time investigation of dynamic events in proteins on the time scale of seconds, Journal of the American Chemical Society 127 (2005) 8014-8015. The perfusion pump 20 is controlled by one of the spare output lines on the Varian Inova console. The pump is switched on before the first steady state scan, and remains on during the perfusion delay. It is then switched off during the bead settling delay. After the first steady state scan, the pulse sequence skips the pump control code. The signals are interpreted by LabView (National Instruments) software, which controls the pump 20. The software also records the pH value at 1 minute intervals. Cells are electrostatically encapsulated into 1 mm diameter $Ca^{2+}$ alginate spheres to keep them in the bioreactor. See C. Dulieu, D. Poncelet, R. J. Neufeld, Encapsulation and immobilization techniques, in: W. M. Kuthreiber, R. P. Lanza, W. L. Chick (Eds.), Cell Encapsulation Technology and Therapeutics, Birkhauser, Boston, 1999, pp. 3-17. The circulation of the encapsulated cells facilitates the delivery of nutrients and waste removal. The bioreactor has two states: pump off (FIG. 2), and pump on (FIGS. 3-4). When the pump is off, encapsulated cells settle into the 8 mm diameter tube for data acquisition (FIG. 2).

When the pump is on, the encapsulates travel from the 8 mm diameter tube into the wider circulation chamber as shown in FIG. 3. The movement of the encapsulates from a narrow to wider tube results in a reduction in pressure causing the encapsulates to circulate in the chamber (FIG. 4). The pulsed, upward motion also prevents the encapsulates from clogging the outlet of the cell chamber. Settling of the encapsulates requires approximately 90 s from the time the pump is turned off.

CEC Bioreactor without Flowing Media

Figure 6:
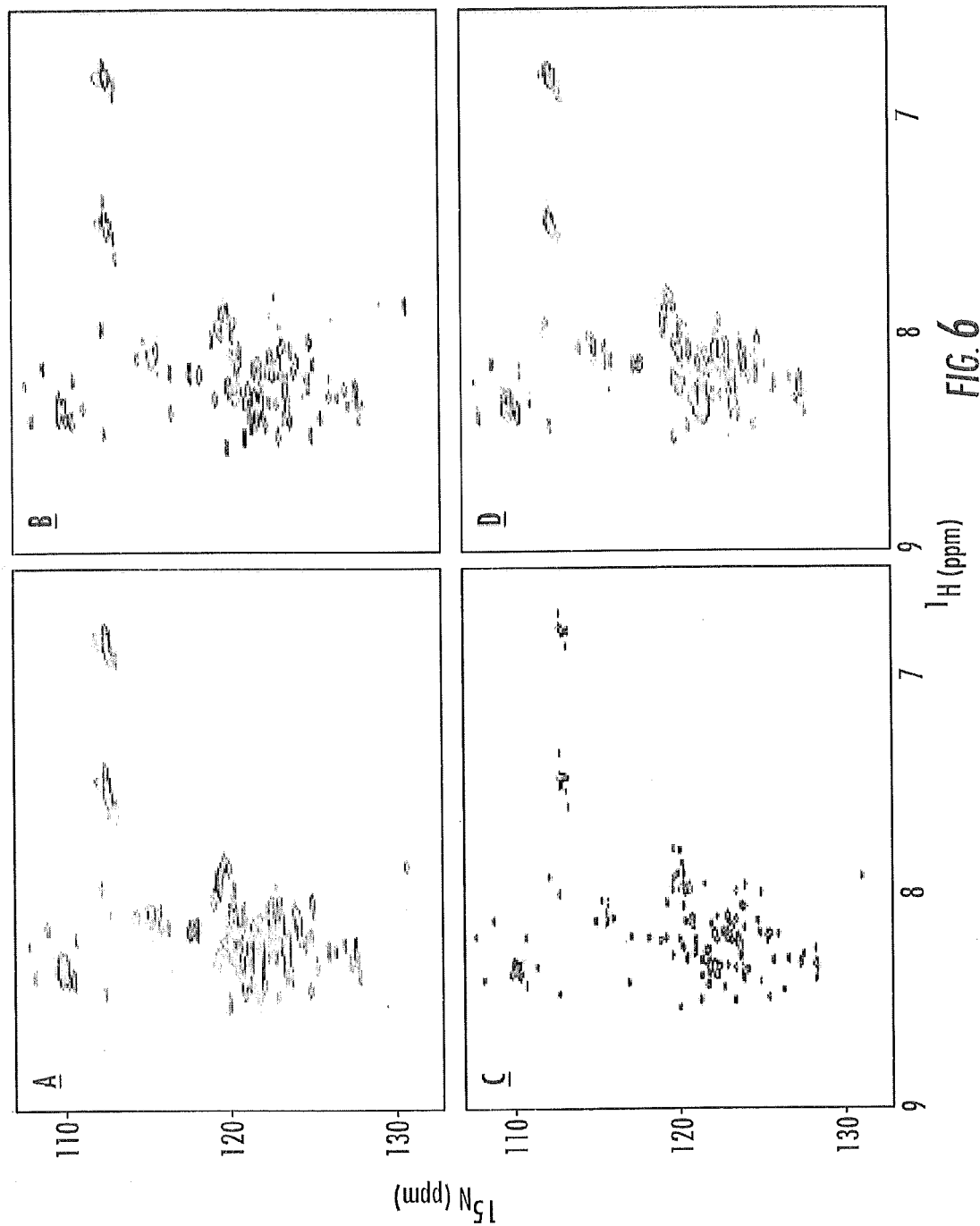
FIGS. 6A-6D are graphs of α-synuclein spectra.

To assess the bioreactor's suitability for in-cell NMR experiments, the $^1H$-$^{15}N$ HSQC spectrum of encapsulated *E. coli* in the bioreactor is compared to the HSQC spectrum of $^{15}N$-enriched α-synuclein obtained in a conventional 5 mm NMR probe (FIGS. 6A and 6B). The in vitro spectrum of purified α-synuclein (FIG. 6C) is shown as a reference. The in vitro spectra were acquired at a lower temperature because it has been shown that the in vitro spectrum acquired at 10° C. is equivalent to in-cell spectra acquired at 37° C. See B. C.

McNulty, A. Tripathy, G. B. Young, L. M. Charlton, J. Orans, G. J. Pielak, Temperature-induced reversible conformational change in the first 100 residues of α-synuclein, Protein Science 15 (2006) 602-608. B. C. McNulty, G. Y. Young, G. P. Pielak, Macromolecular crowding in the *Escherichia coli* periplasm maintains α-synuclein disorder, Journal of Molecular Biology 355 (2006) 893-897. The similarity of the spectra in FIGS. 6A-6D indicates that α-synuclein can be detected in the bioreactor. To assess the bioreactor's effect on spectral quality, the in-cell HSQC spectrum of encapsulated *E. coli* expressing $^{15}$N-enriched α-synuclein in the bioreactor is compared to the HSQC spectrum of the same encapsulates in a 5 mm tube (FIGS. 6A and 6D). The spectrum of the encapsulated cells in the 5 mm tube is consistent with the published spectrum. See C. Li, L. M. Charlton, A. Lakkavaram, C. Seagle, G. Wang, G. B. Young, J. M. Macdonald, G. J. Pielak, Differential dynamical effects of macromolecular crowding on an intrinsically disordered protein and a globular protein: implications for in-cell NMR spectroscopy, Journal of the American Chemical Society 130 (2008) 6310-6311. The crosspeaks broaden when encapsulates are placed in the bioreactor, but the quality of spectra is only slightly degraded.

CEC Bioreactor with Flowing Media

Figure 7:
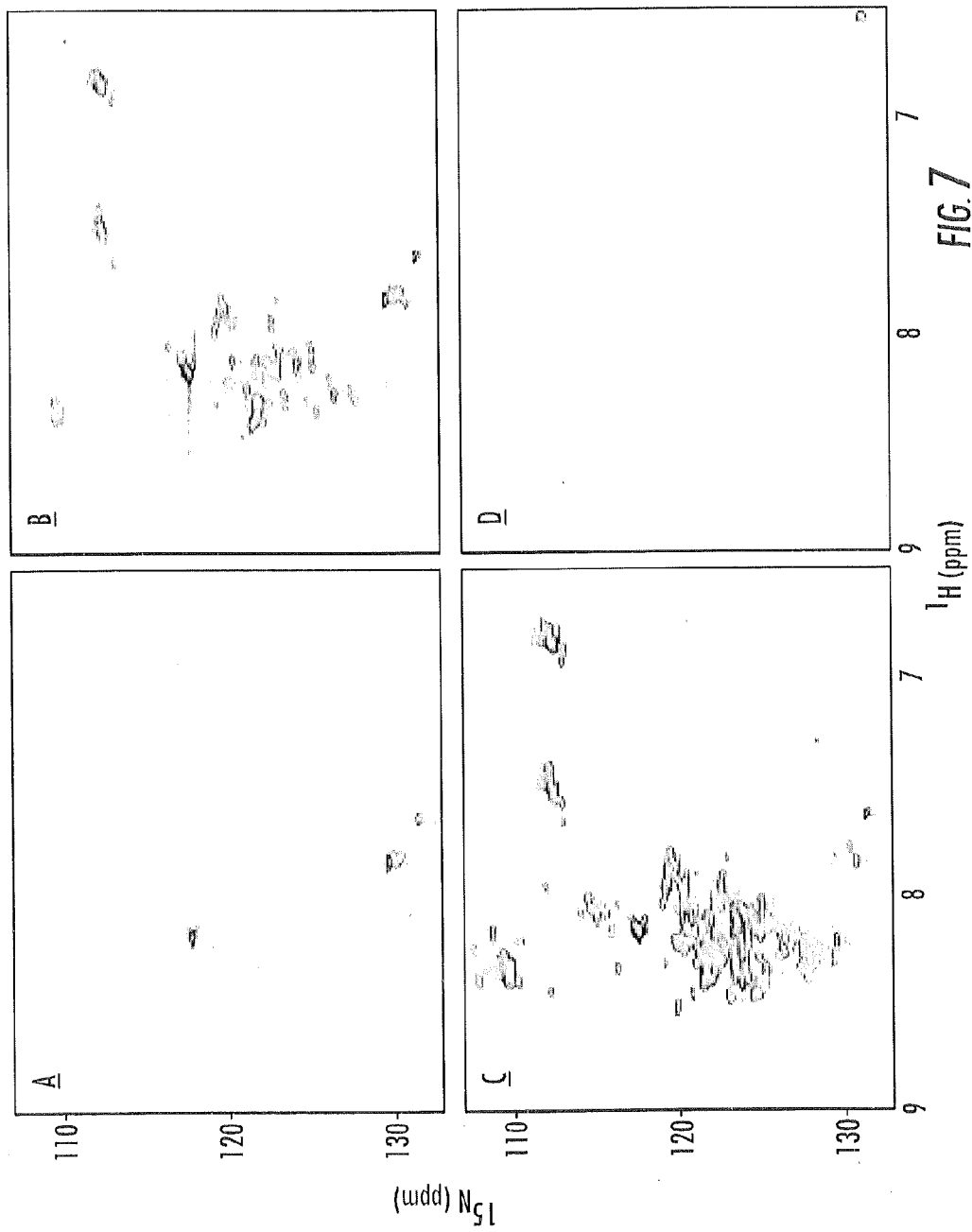
FIGS. 7A-7D are graphs of in-cell SOFAST 15N-1H HMQC spectra (37° C.) of *E. coli* expressing α-synuclein in the bioreactor.

The expression of α-synuclein was monitored with the $^1$H-$^{15}$N SOFAST HMQC pulse sequence, rather than the HSQC sequence, to obtain better time resolution. Spectra as a function of time are shown in FIGS. 7A-7C. The spectrum of the encapsulates before induction (FIG. 7A) has few crosspeaks and no unambiguous α-synuclein crosspeaks. After induction new crosspeaks begin to appear. With each successive spectrum, the crosspeaks increase in volume as seen at four and eighteen hours (FIGS. 7B and 7C). Using methods described by Slade et al., the intracellular concentration of α-synuclein was determined to be 0.8 mM at eighteen hours. See K. M. Slade, R. Baker, M. Chua, N. L. Thompson, G. J. Pielak, Effects of recombinant protein expression on green fluorescent protein diffusion in *Escherichia coli*, Biochemistry 48 (2009) 5083-5089.

As a control, the encapsulates were removed after the experiment and a spectrum was acquired of the surrounding media (FIG. 7D). The spectrum shows only a weak crosspeak, indicating that the bulk of the signal comes from the encapsulated cells. The viability of the *E. coli* in the bioreactor experiments was determined by plating serial dilutions of dissolved encapsulates before and after each experiment. The viability was 95%. The pH of the medium perfused around the encapsulated cells remained at 7.00 for the duration of the experiment.

Figure 8:
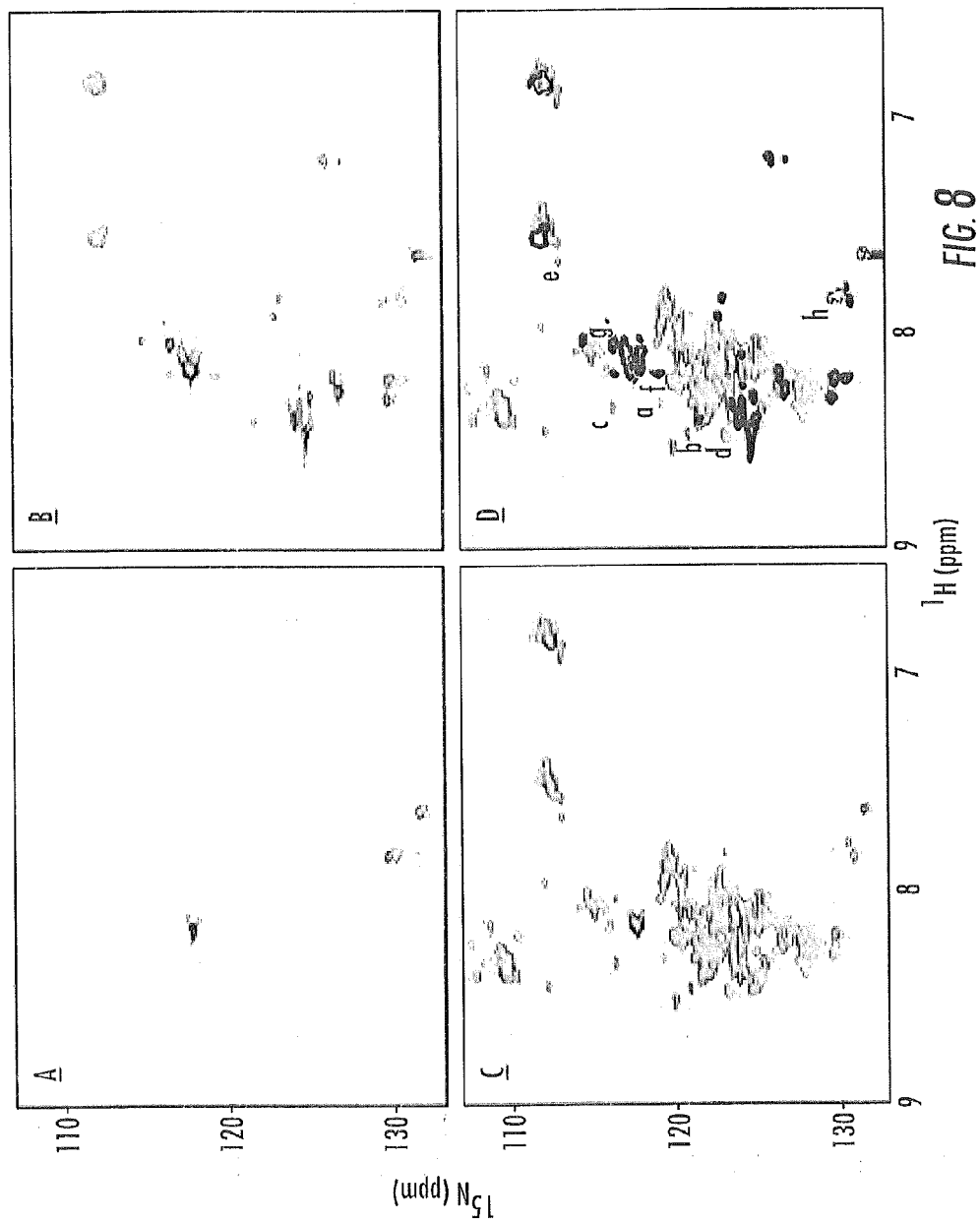
FIGS. 8A-8D Determining which crosspeaks correspond to α-synuclein.
Figure 9:
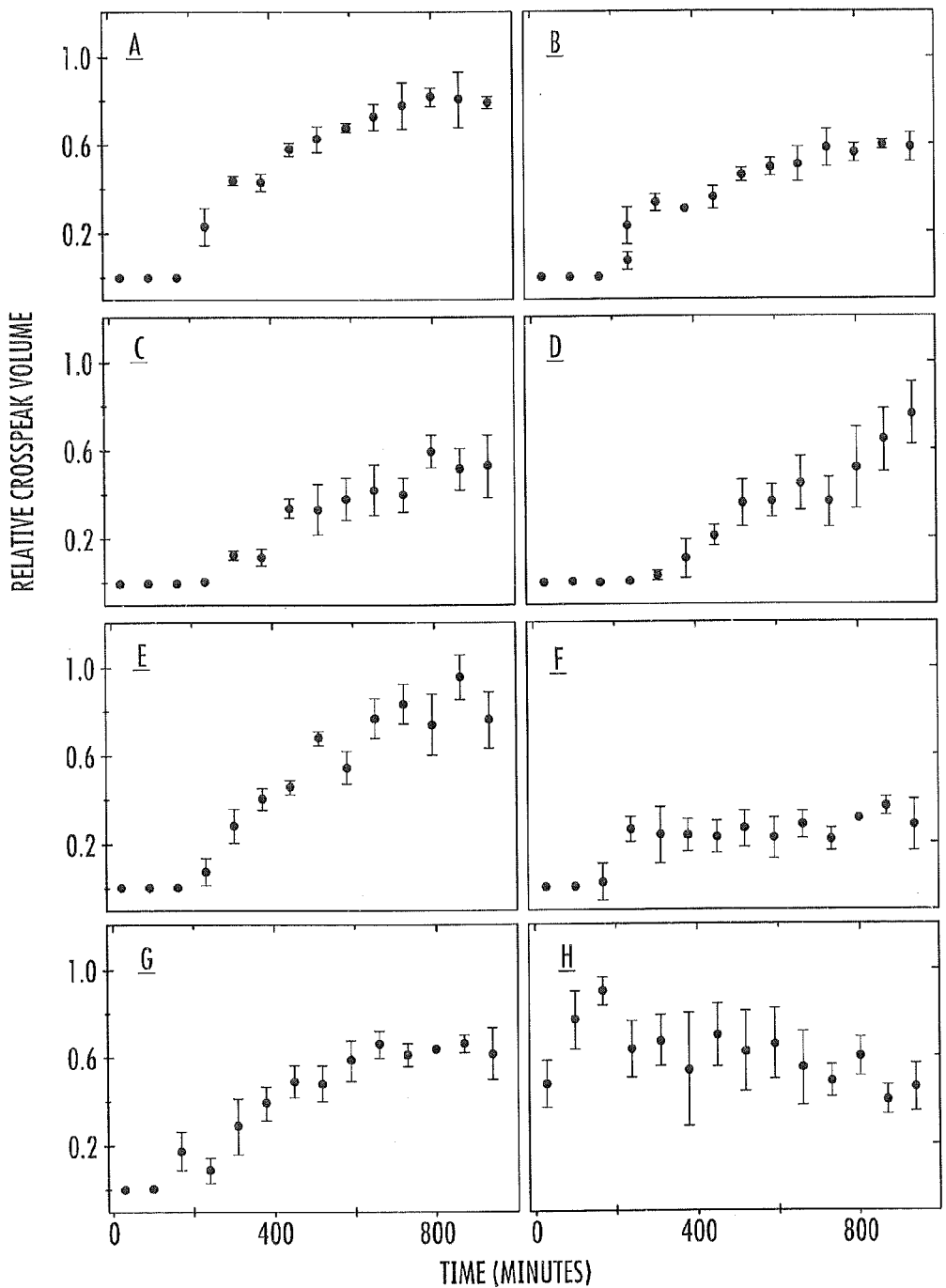
FIGS. 9A-9H are graphs of temporal changes in crosspeak volume after inducing α-synuclein expression in the bioreactor.

Although the CEC bioreactor provides an environment where encapsulated *E. coli* cells express α-synuclein, a sacrifice of spectral resolution for increased time resolution made it difficult to distinguish between metabolites and protein crosspeaks. To determine which crosspeaks corresponded to α-synuclein, spectra of fresh media were collected (FIG. 8A) and of *E. coli* containing a pUC18 plasmid without the α-synuclein gene (FIG. 8B). See J. Vieira, J. Messing, The pUC plasmids, an M13mp 7-derived system for insertion mutagenesis and sequencing with synthetic universal primers, Gene 19 (1982) 259-268. Overlaying these spectra with the spectrum of α-synuclein expressed in the bioreactor (FIG. 8C) shows that most of the crosspeaks are from α-synuclein (FIG. 8D). The overlay the quantification of temporal changes in crosspeak volumes as shown in FIGS. 9A-9H. The crosspeak from the defined minimal media is the only crosspeak detectable at 30 minutes (FIG. 9H). Although induction occurred at 30 minutes, there was a lag phase of approximately four hours before crosspeaks could be detected (FIGS. 9A, 9B and 9E-9G). Some crosspeaks are not detectable until approximately seven hours (FIGS. 9C and 9D).

The volumes of α-synuclein crosspeaks increased with time, beginning with a lag phase before growing exponentially to a plateau (FIG. 9A-9E). One crosspeak deviated from this trend (FIG. 9D), most likely because of the poor resolution in this area of the spectrum (FIG. 9D). Temporal changes in crosspeak volumes for two metabolites showed different trends. One metabolite remained constant (FIG. 9F), while the other metabolite showed a time dependence that resembled the α-synuclein crosspeaks (FIG. 9G). The crosspeak from the defined minimal media is the only crosspeak that showed a slight decrease in intensity with time (FIG. 9H).

Discussion

The CEC bioreactor described above may provide a controlled environment for NMR experiments involving living cells. The bioreactor is configured to allow media to deliver nutrients and remove waste from encapsulated cells contained in a circulation chamber. When the flow of media is stopped, the encapsulated cells settle, which allows data acquisition.

In the experimental setup, the CEC bioreactor is the only component located inside the spectrometer. This configuration allows the external components to be altered without removing the bioreactor before or during the experiment, facilitating studies requiring different conditions in one experiment. The setup is also versatile. Different solution probes and sensors can be inserted between the external components. The tubing can be rerouted, for example, to send the media to a waste container. In addition, the material used to make the bioreactor can be changed for experiments requiring different isotopic nuclei detection. Teflon for $^1$H-$^{15}$N detection was used, but a Plexiglass bioreactor can be used for $^{19}$F NMR.

The CEC bioreactor is suitable for protein in-cell NMR experiments (FIGS. 6A and 6B). The design provides an environment where encapsulated cells can express protein while maintaining reasonably high quality in-cell NMR spectra (FIGS. 6C and 6D). Furthermore, the bioreactor can be used to quantify temporal changes in crosspeak volumes during the experiment (FIGS. 7A-7D and 8A-8D).

It was shown that α-synuclein was present at an intracellular concentration of 0.8 mM at eighteen hours. Using information from FIGS. 9A-9F, it was concluded that the detection limit for in-cell NMR is approximately 0.1 mM. This finding is consistent with other work on the minimal intracellular protein concentration needed for in-cell NMR. See Z. Serber, W. Straub, L. Corsini, A. M. Nomura, N. Shimba, C. S. Craik, P. Ortiz de Montellano, V. Dötsch, Methyl groups as probes for proteins and complexes in in-cell NMR experiments, Journal of the American Chemical Society 126 (2004) 7119-7125. For most residues, the detection limit is achieved after three hours. Two protein crosspeaks do not follow this trend in that they are not detectable until approximately seven hours (FIGS. 9C and 9D). The crosspeaks from glycine residues that comprise the ear-shaped pattern in the upper left region of α-synuclein as shown in FIGS. 7A-7D ($^{15}$N ppm 108-113, $^1$H ppm 8.3-8.7) follow a similar trend. The delay in detectability may be due to differential binding of α-synuclein to other intracellular components, which broadens the crosspeaks. Another possibility for the delay is differential relaxation because in vitro models for α-synuclein dynamics show that certain residues experience less mobility. See B. C. McNulty, G. Y. Young, G. P. Pielak, Macromolecular crowding in the *Escherichia coli* periplasm maintains α-synuclein disorder, Journal of Molecular Biology 355 (2006) 893-897.

Decreased mobility produces broader, weaker signals, which would explain the longer time required to detect them.

In summary, the CEC bioreactor provides a controlled environment where protein NMR spectra data can be acquired in living *E. coli* cells. However, the CEC bioreactor may be compatible with other cell types, and may be versatile enough for metabolomic as well as protein experiments. Eukaryotic cells, whose viability is adversely affected by current NMR methods, may also be used. One possible goal is to monitor temporal changes in protein structure and metabolism due to perturbations, such as drug interactions, in human cells, and so increase the understanding of intracellular components under physiological conditions.

Experimental

Purification of Wild Type α-Synuclein for In Vitro Experiments

The pT7-7 plasmid containing the α-synuclein gene was transformed into *E. coli* Bl-21 (DE3) Gold cells (Strategene). Plasmid containing cells were selected with 0.1 mg/mL, ampicillin. A 5 mL overnight culture was grown from a single colony and used to inoculate a 50 mL culture of Spectra 9 $^{15}$N-enriched media (Cambridge Isotope Laboratories) at 37° C. in a rotary shaker (225 rpm, New Burnswick Scientific, Model 1-26). The saturated overnight culture was used to inoculate 1 L of M9 minimal media (Z. Serber, R: Ledwidge, S. M. Miller, V. Dötsch, Evaluation of parameters critical to observing proteins inside living *Escherichia coli* by in-cell NMR spectroscopy, Journal of the American Chemical Society 123 (2001) 8895-8901) containing 1 g/L $^{15}$NH$_4$Cl. After reaching an absorbance at 600 nm (A600) of 0.8-1.0, the culture was induced with isopropyl b-D-thiogalactopyranoside (IPTG) to a final concentration of 1 mM. The culture was placed in the rotary shaker (225 rpm) at 37° C.

After five hours the cultures were pelleted using a swinging bucket centrifuge (Sorvall RC-3B, H6000A rotor) at 1600 g for 30 minutes at 4° C. and the pellet was stored at 20° C. The pellet was resuspended in 30 mL of lysis buffer (50 mM Tris, 150 mM NaCl, 1 mM phenylmethanesulfonyl fluoride, 0.4 g/L lysozyme, pH 8.0). RNase and DNase were added to a final concentration of 0.02 g/L each.

The samples were stirred (250 rpm) at 4° C. for 20 minutes. The lysate was sonicated (Branson Ultrasonics, Fischer Scientific) continuously for five minutes, boiled in a water bath for 20 minutes, and then centrifuged at 13,000 g for 30 minutes at 4° C. (SS-34 rotor). The supernatant was subjected to streptomycin sulfate precipitation (10 g/L) and centrifuged for 30 minutes at 4° C. The supernatant was subjected to (NH4)2SO4 precipitation (361 g/L) and centrifuged again for 30 minutes at 4° C. The pellet was resuspended in 20 mM sodium phosphate buffer (pH 7.4) and dialyzed (Thermo Scientific, 3500 MWCO) overnight, with stirring at 4° C., against the same buffer.

The protein was further purified by anion exchange chromatography (GE Healthcare, Q Sepharose HiPrep 16/10 column) with a 0-1 M linear gradient of NaCl in 20 mM phosphate buffer (pH 7.4). Fractions were subjected to SDS-PAGE on an 18% gel with Coomassie brilliant blue staining. Fractions containing α-synuclein were pooled and dialyzed against water overnight, with stirring, at 4° C. The protein was concentrated in an YM-3 Centricon filter (Millipore, MWCO 3500) using centrifugation at 1000 g (SS-34 rotor) for one hour at 4° C. The purity of the protein was determined by SDS-PAGE with Coomassie staining. The pure α-synuclein was lyophilized (Labconco) and stored at 20° C. The yield was 35-60 mg of pure α-synuclein per liter of saturated cell culture.

Cultivation of *E. coli* for In-Cell NMR Experiments

A 5 mL overnight culture was grown from a single colony and used to inoculate a 500-mL Erlenmeyer flask containing 50 mL of isotopically enriched media, as described above. After the culture reached an A600 of 0.8-1.0, the cells were induced with IPTG to a final concentration of 1 mM. Expression was allowed to proceed for four hours. The cells were gently harvested by using the swinging bucket centrifuge for 30 minutes at 4° C. The pellet was resuspended in 1 mL of spent media.

Cultivation and Encapsulation of *E. coli* for NMR Bioreactor Experiments

A 5 mL overnight culture was grown from a single colony as described above and used to inoculate 150 mL of Luria Broth (10 mg/mL Tryptone, 5 mg/mL yeast extract, 10 mg/mL NaCl) at 37° C. The culture was grown in the rotary shaker (225 rpm) to an A600 of 0.8-1.0. The cells were gently harvested in the swinging bucket centrifuge for 20 minutes at 4° C. and resuspended in 1 mL of spent media. The resuspended cells were mixed with a 2% w/v alginate (Sigma) solution in 20 mM phosphate, 150 mM NaCl (pH 7.4) to give a final concentration of 1% alginate (50:50 mixture alginate: cell slurry).

The electrostatic encapsulation device (not shown) included a 1 mL insulin syringe (BD), a 24 gauge winged angiocatheter (0.7×19 mm tip, Braun), a 23 gauge needle (BD), a syringe pump (Braintree Scientific 8000), and an adjustable high voltage power supply (Spellman SL10). The insulin syringe, equipped with the needle, was loaded with the cell/alginate mixture. The other needle, which was inserted horizontally through the center of the angiocatheter, was connected to the positive pole of the power supply. The negative pole of the power supply was placed into the 150 mM CaCl$_2$ solution. The syringe containing the mixture was inserted into the top of the angiocatheter and placed onto the pump. The syringe pump was set to a rate of 0.714 mL/min, the power supply voltage to 3.35 kV, and the stir-plate to approximately 300 rpm. The tip of the angiocatheter was centered 1.2 cm above a 250 mL beaker containing 150 mL of 150 mM CaCl$_2$. The mixture was forced through the tip of the angiocatheter and streamed into the CaCl$_2$ solution.

The Ca$^{2+}$ polymerizes the alginate which, in turn, forms encapsulated beads containing the cells. The encapsulated cells were retrieved with suction and placed in a 15 mL Falcon tube containing 150 mM CaCl$_2$ solution for transport to the NMR spectrometer. The CaCl$_2$ solution was removed and the encapsulated cells were washed with the phosphate-free minimal medium. The phosphate-free minimal medium consisted of 100 mM HEPES (pH 7.4), 150 mM CaCl$_2$, phosphate-free M$_9$ salts [1 mg/mL $^{15}$NH$_4$Cl, 2 mM MgCl$_2$, 11 g/mL thiamine, 2% v:v10×$^{15}$N-enriched Bioexpress 1000 media (Cambridge Isotope Laboratories)] and 0.1 mg/mL ampicillin. After washing, the encapsulated cells were placed inside the bioreactor, which was then placed into the spectrometer.

After acquiring the initial spectrum, lactose was added to a final concentration of 1% w/v. The lactose acts as an inducer and the sole carbon source. For each spectrum, the pump circulated medium through the system at a rate of 45 mL/min for 30 minutes. Five minutes were allotted for the encapsulated cells to settle into the detection region of the bioreactor. As a control the procedure was repeated for *E. coli* containing the pUC18 plasmid.

NMR

Data were acquired at the UNC Biomolecular NMR facility on a Varian Inova 600 MHz NMR spectrometer. Data were processed and visualized with NMRpipe and NMRviewJ, respectively. See Z. Serber, R. Ledwidge, S. M. Miller, V. Dötsch, Evaluation of parameters critical to observing proteins inside living *Escherichia coli* by in-cell NMR spectroscopy, Journal of the American Chemical Society 123 (2001) 8895-8901. Samples for dilute solution spectra comprised a 90:10 (v:v, pH 7.4) mixture of purified 200 lM α-synuclein solution: $D_2O$ in a standard 5 mm NMR tube. $^1H$-$^{15}N$ HSQC spectra were acquired at 10° C. with a 5 mm Varian Triax triple resonance probe ($^1H$ sweep width: 11990.40 Hz; $^{15}N$ sweep width: 2100 Hz, eight transients, 128 increments). Each spectrum was acquired in about 35 minutes. See B. C. McNulty, A. Tripathy, G. B. Young, L. M. Charlton, J. Orans, G. J. Pielak, Temperature-induced reversible conformational change in the first 100 residues of α-synuclein, Protein Science 15 (2006) 602-608.

Samples for simple in-cell NMR experiments included a 90:10 (v:v) mixture of resuspended cells: $D_2O$ in a standard 5 mm NMR tube. $^1H$-$^{15}N$ HSQC spectra were acquired as described above, except with 12 transients and 128 increments. Each spectrum was acquired in about one hour. See G. Bodenhausen, D. J. Ruben, Natural abundance nitrogen-15 NMR by enhanced heteronuclear spectroscopy, Chemical Physics Letters 69 (1980) 185-189; L. Kay, P. Keifer, T. Saarinen, Pure absorption gradient enhanced heteronuclear single quantum correlation spectroscopy with improved sensitivity, Journal of the American Chemical Society 114 (1992) 10663-10665.

Samples for encapsulated in-cell NMR experiments comprised encapsulates in a 90:10 (v:v) mixture of 150 mM $CaCl_2$: $D_2O$ in a standard 5 mm NMR tube. For encapsulates in standard 5 mm NMR tubes, $^1H$-$^{15}N$ HSQC spectra were acquired as described above. In the bioreactor, $^1H$-$^{15}N$ HSQC spectra were acquired unlocked at 37° C. with an 8 mm modified Varian Triax triple resonance z-gradient probe as described above. Samples for NMR bioreactor experiments comprised encapsulated cells in phosphate-free media supplemented with Bioexpress 1000. $^1H$-$^{15}N$ SOFAST HMQC spectra were acquired at 37° C. as described above, except with 48 transients and 96 increments. The spectra were acquired unlocked due to the adverse effects of $D_2O$ on cell growth and protein expression. Each spectrum required 35 minutes.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A device for nuclear magnetic resonance (NMR) analysis of particulate materials comprising:
   a detector chamber configured for insertion into an NMR spectrometer and configured to receive particulate materials in a fluid, the detector chamber having a first end and a second end;
   a circulation chamber attached to and in fluid communication with the first end of the detector chamber;
   a transition region between the detector chamber and the circulation chamber; and
   a fluid supply interface at the second end of the detector chamber that is configured to attach to a fluid source,
   wherein the detector chamber, the circulation chamber and the transition region are sized and configured such that, when fluid flows from the fluid supply interface into the second end of the detector region, a circulating current is formed in the transition region and/or the circulation chamber such that the particulate matter is contained in the circulation chamber by the circulating current.

2. The device of claim 1, wherein the circulating current substantially prevents particulate material from entering the detector chamber when fluid flows from the fluid supply interface.

3. The device of claim 1, wherein the fluid flowing from the fluid supply interface forms a reduced pressure region in the transition region and/or the circulation chamber.

4. The device of claim 1, wherein the detector chamber is sized and configured such that, when a fluid in the detector chamber is generally static, the particulate material is contained in the detector chamber.

5. The device of claim 1, wherein the particulate material is an encapsulated cell and the fluid is a perfusion medium.

6. The device of claim 1, wherein the fluid supply interface is configured to connect to a pump that supplies fluid from the fluid source to the detector chamber to form the reduced pressure region.

7. The device of claim 1, wherein the circulation chamber has a cross-sectional area that is larger than a cross-sectional area of the detector chamber.

8. The device of claim 1, wherein the transition region connects the circulation chamber and the detector chamber at an angle between about 30 and 60 degrees.

9. A method for NMR imaging of particulate matter in a fluid, the method comprising:
   providing a device comprising:
      a detector chamber configured for insertion into an NMR spectrometer and configured to receive particulate materials in a fluid, the detector chamber having a first end and a second end;
      a circulation chamber attached to and in fluid communication with the first end of the detector chamber;
      a transition region between the detector chamber and the circulation chamber; and
      a fluid supply interface at the second end of the detector chamber that is configured to attach to a fluid source,
   acquiring nuclear magnetic resonance (NMR) signal from particulate material in the detector chamber; and then
   supplying fluid flow into the second end of the detector region to form a circulating current in the transition region and/or the circulation chamber such that the particulate matter is contained in the circulation chamber by the circulating current.

10. The method of claim 9, wherein the circulating current substantially prevents particulate material from entering the detector chamber when fluid flows from the fluid supply interface.

11. The method of claim 9, wherein the fluid flowing from the fluid supply interface forms a reduced pressure region in the transition region and/or the circulation chamber.

12. The method of claim 9, wherein the detector chamber is sized and configured such that, when a fluid in the detector chamber is generally static, the particulate material is contained in the detector chamber.

13. The method of claim 9, wherein the particulate material is an encapsulated cell and the fluid is a perfusion medium.

14. The method of claim 9, wherein the fluid supply interface is configured to connect to a pump that supplies fluid from the fluid source to the detector chamber to form the reduced pressure region.

15. The method of claim 9, wherein the circulation chamber has a cross-sectional area that is larger than a cross-sectional area of the detector chamber.

16. The method of claim 9, wherein the transition region connects the circulation chamber and the detector chamber at an angle between about 30 and 60 degrees.

* * * * *